United States Patent [19]

Schwartz

[11] 4,147,662
[45] Apr. 3, 1979

[54] FILM HOLDER

[76] Inventor: Robert Schwartz, 1271 Westfield Ave., Rahway, N.J. 07090

[21] Appl. No.: 831,971

[22] Filed: Sep. 9, 1977

Related U.S. Application Data

[63] Continuation-in-part of Ser. No. 725,678, Sep. 22, 1976, abandoned.

[51] Int. Cl.² .................. G03B 41/16; A61B 6/04; A61B 6/14
[52] U.S. Cl. ............................ 250/444; 250/452; 250/479
[58] Field of Search ............ 250/444, 452, 490, 491, 250/479, 478

[56] References Cited

U.S. PATENT DOCUMENTS 3,792,281   2/1974   Schwartz et al. .................. 250/452

FOREIGN PATENT DOCUMENTS 257575   4/1949   Switzerland .................. 250/479

Primary Examiner—Alfred E. Smith
Assistant Examiner—T. N. Grigsby

[57] ABSTRACT

Reproducible panoramic x-ray photographs of the dental arches are secured with a portable film holder apparatus that is used in conjunction with an independent x-ray camera unit. The film holder is composed of a photographic plate holder assembly used in combination with a sectional photographic plate shield assembly and an x-ray camera aiming system.

4 Claims, 5 Drawing Figures

FILM HOLDER

CROSS-REFERENCE TO RELATED APPLICATION

This application is a Continuation-in-part of Ser. No. 725,678, filed Sept. 22, 1976. and now abandoned.

BACKGROUND OF THE INVENTION

This invention relates to an apparatus for producing a panorammic x-ray photograph of a human dental arch structure. More particularly, this invention relates to an apparatus for securing panoramic x-ray photographs from sequentially obtained independent x-ray photographs of segments of the patient's upper and lower arch structure.

DESCRIPTION OF THE PRIOR ART

This invention is an improved version of the device described in U.S. Pat. No. 3,792,281. The aforesaid patent describes an apparatus for producing panoramic dental arch x-ray photographs. Other devices useful in obtaining panoramic x-ray photographs have been disclosed in the prior art. Representative examples of such devices are disclosed in U.S. Pat. No. 3,536,915; U.S. Pat. No. 3,636,349 and U.S. Pat. No. 3,617,742.

SUMMARY OF THE INVENTION

The device of the present invention permits formation of reproducible panoramic x-ray photographs of the dental arches using an independent x-ray camera. The device of the present invention comprises (i) a photographic plate holder assembly that locates and positions a photographic plate, preferably a unitary photographic plate, (ii) a sectional shield assembly that is adapted to engage the photographic plate holder assembly and (iii) and x-ray camera aiming system. A reprducible panoramic x-ray photograph is secured by aligning the patient's dental arches with the aiming system associated with the device and then sequentially removing and replacing portions of the sectional shield assembly and taking x-ray photographs of the patient's dental anatomy with an independent x-ray camera in such a manner as to expose the unshielded portion of the photographic plate. Normally, an acceptable reproducible panoramic x-ray photograph can be secured from the independent, abutting x-ray exposures of various portions of the patient's dental anatomy.

DESCRIPTION OF THE DRAWINGS

The invention will be better understood by reference to the accompanying drawing wherein:

The photographic plate, which is encased within flexible pouch 30, is maintained in position and shielded from x-ray exposure by means of a multi-component or sectional shield assembly. At least one lateral surface of the shield members is formed of an x-ray impervious material, e.g. lead. The shield assembly is made up of side arch shields 40 and 41 and central shield member 42. As shown in FIG. 1 only one central shield member is employed; however, it is within the purview of the instant invention to employ additional central plane shield members. Shield members 40, 41 and 42 serve to cover the photographic plate that is positioned within the holder assembly to prevent the exposure of the photographic plate. At least one of the lateral surfaces of shield members 40, 41 and 42 serve to position the photographic plate 30 within the plate holder assembly and, in the case of side arch shield members 40 and 41, function to position the photographic plate in a non-shielded arch structure corresponding to the facial contour of the patient facing the holder assembly. Desirably, shield members 40 and 41 possess a slightly curved surface.

Figure 1:
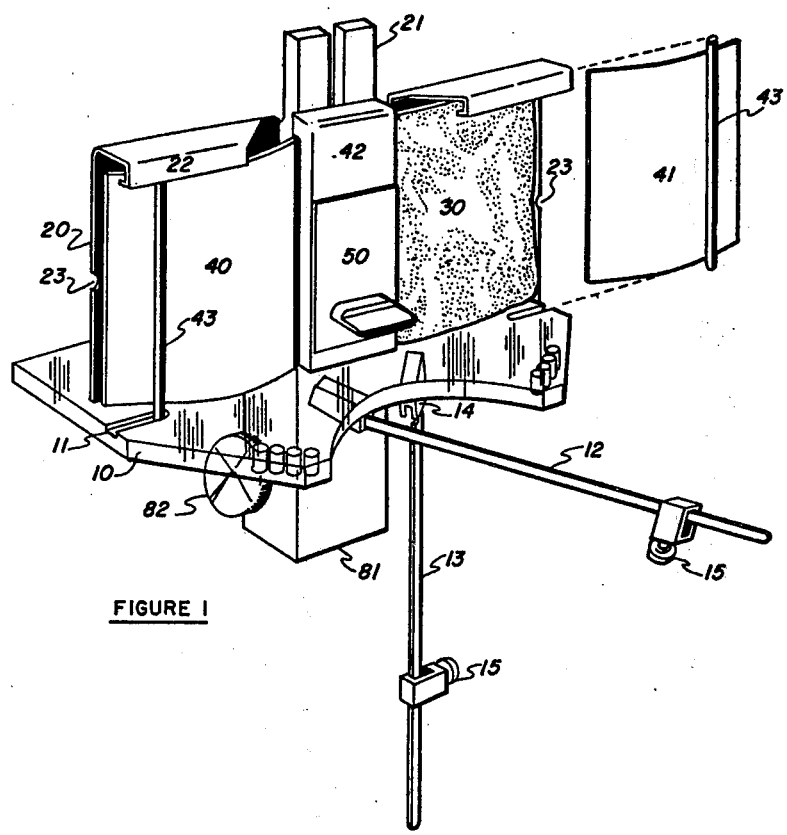
FIG. 1 is a perspective view showing the film holding apparatus with one of the shield members in a removed position and the left aiming bar of the camera aiming system in the raised stop position.

To the frontal portion of each side arch shield member 40 and 41 is attached rod member 43. Rod member 43 serves to assist in the positioning of side arch members 40 and 41 within the downwardly extending lip member 22 of the photograhic plate holder assembly. Shield members 40 and 41, when in position, rest upon the upper surface of base member 10 and are maintained in shielding position by means of rod members 43 that slide within track guides 11 that are machined into the upper surface of the base member and the downwardly extending lip 22 of the photographic plate holder assembly. When in shielding position, the segments of the shield assembly are present in a lap-joint relationship, that is, side arch shield members 40 and 41 extend beneath (or over) the outer edge of central shield member 42.

Figure 5:
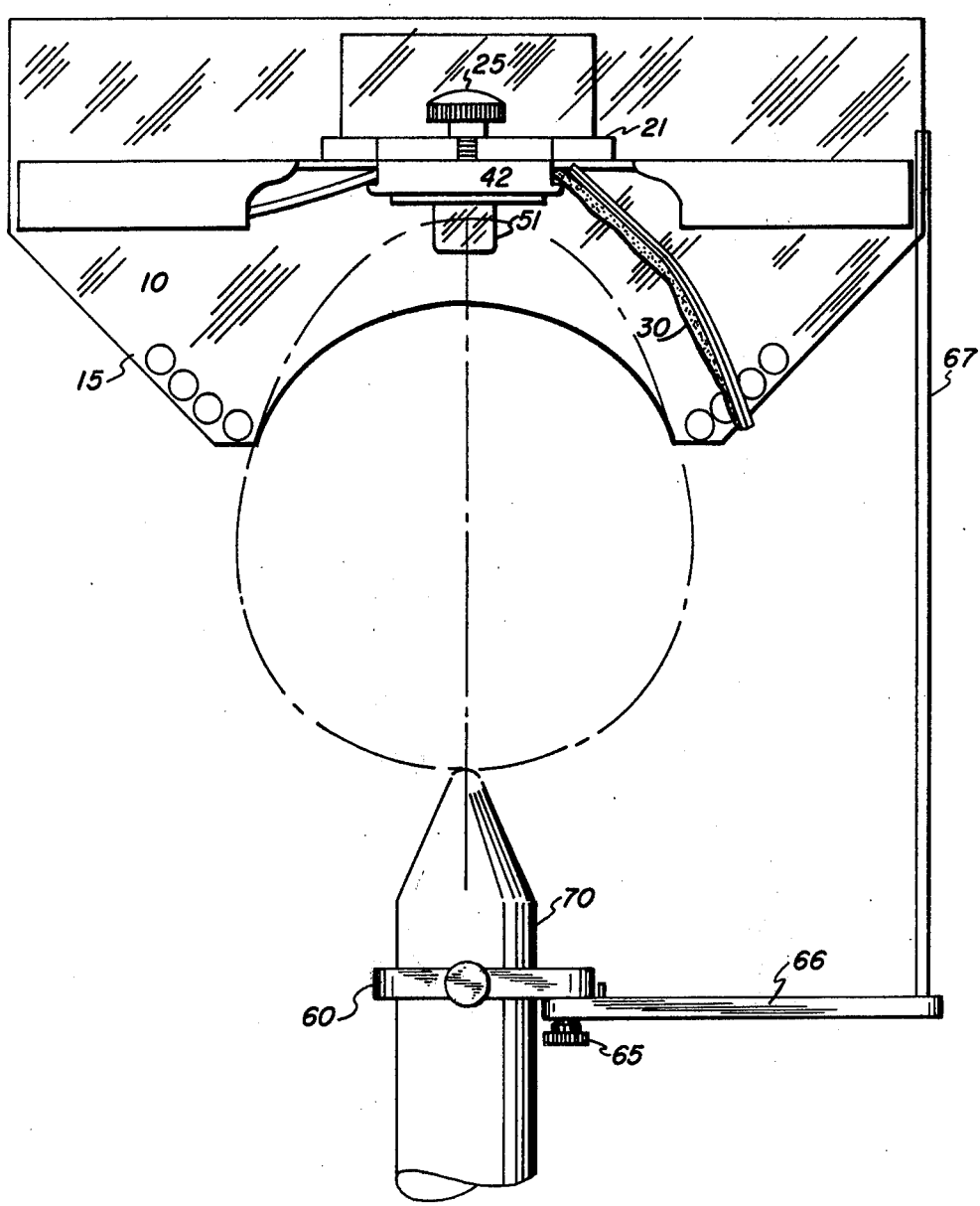
FIG. 5 is a horizontal top view of the assembly of the present invention with the x-ray camera cone in position for securing a photograph of the central portion of the arch structure. The above-described drawings show preferred embodiments of the present invention. The film holding apparatus is composed, first of all, of a base member 10 having upper and lower surfaces. Desirably, the base member is essentially flat and has mounted on the upper surface thereof a photographic plate holder assembly and a sectional shield assembly that is adapted to engage the photographic plate holder assembly to cover a unitary photographic plate that is contained within pouch 30. Pouch 30 is positioned within the plate holder assembly. The plate holder assembly is made up of plate holder 20 which is perpendicularly affixed to the upper surface of base member 10. The plate holder 20 is maintained in vertical alignment by means of standard 21 which is also positioned on the top surface of base member 10. As can be seen from the figures, the plate holder 20 comprises a flat planar member that is provided with a downwardly extending lip member 22 that extends along at least a portion of the top margin of the flat planar member. The frontal portion of the photographic plate holder assembly is adapted to permit the x-ray exposure of the photographic plate (contained within pouch 30) that is positioned in close proximity to the planar portion of plate holder assembly 20. Typically, the length and width dimensions of photographic plate contained within pouch 30 correspond to or are less the length and width dimensions of plate holder 20.

Another segment of the present film holding apparatus is a positioning member 50 that is adapted to locate the upper and lower arches of the patient in a position facing and congruent with the frontal, open portion of the plate holder assembly that contains the photographic plate. Positioning member 50 is preferably formed from a disposable or sterilizable material and, desirably, can be removed from position from shield member 42. In a preferred embodiment, positioning member 50 is slidably engaged upon studs 51 (FIG. 5). Preferably, as shown in the figures, the arch positioning member is located on the central shield member. However, other types of arch positioning members can be used. For example, a positioning member that is formed from an x-ray translucent material could be located on base member 10 rather than on the central shield member 42. In use, the patient grasps positioning member 50 between his maxillary and mandibular arches and maintains this position while the individual x-ray photograhs are taken.

Figure 2:
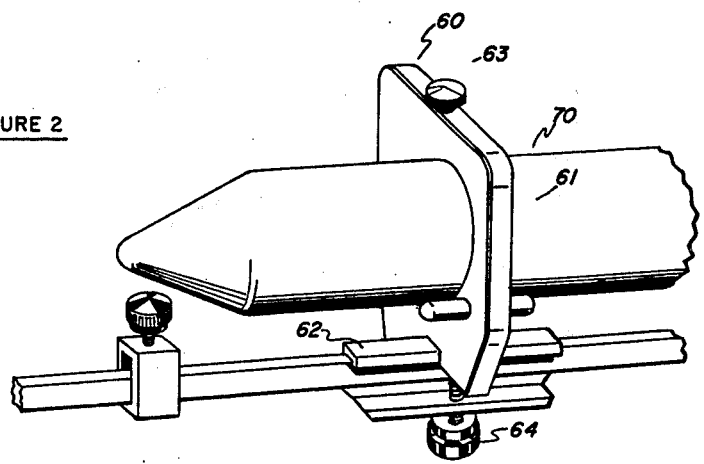
FIG. 2 is a perspective view of the aiming bar locator in position on an x-ray camera cone.
Figure 3:
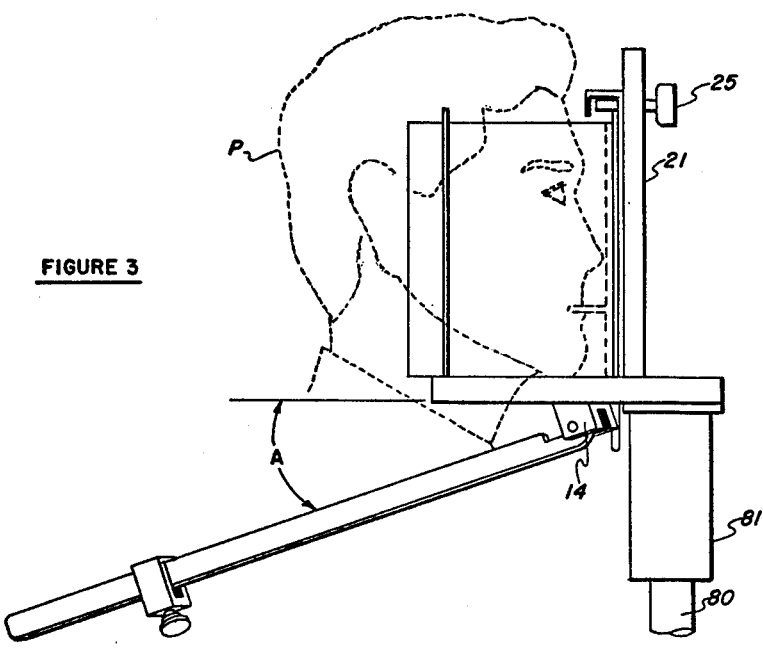
FIG. 3 is a side elevation view of the film holding apparatus of the present invention with one aiming bar in the raised stop position.

Another segment of the film holding apparatus of the present invention comprises means located on base member 10 to locate x-ray camera cone 70 in proper photographing position. The aiming system comprises left aiming bar 12 and right aiming bar 13. The inner end of aiming bars 12 and 13 are pivotably affixed within housings 14 to the lower surface of base member 10. Aiming bars 12 and 13 in the rest position (see aiming bar 13 in FIG. 1), extend downwardly from base member 10. Each of the aiming bars are adapted to be swung upwardly from the rest position to a stop position. The inner end of the aiming bars and/or the housings 14 are adapted, by any suitable means, to alternatively lock the aiming bars in the stop position and to permit their release to the rest position. At the stop position the aiming bar forms an angle A (See FIG. 3) of about 15° below the horizontal and also inscribe an angle B (see FIG. 4) of about 40 to 60, preferably 45° to 55° with an imaginary vertical plane bisecting the central shield member 42. The x-ray camera is brought into proper picture-taking position for pictures of the left and right side arch structure of the patient's dentition by use of the aiming bar locator means 60. Aiming bar locator means 60 consists of cone element 61, channel 62, set screws 63, 64 and 65, extension element 66 and rod member 67. Extension element 66 and rod member 67 are used when an x-ray picture is taken of the central portion of the patient's arch structure. cone element 61 is located on and about the outer periphery of the cone 70 of a typical dental x-ray camera. Cone element 61 is maintained in position on cone 70 with set screw 63 which is threaded through cone element 61 and bears against the outer surface of cone 70. Cone element 61 carries channel 62 and maintains the internal longitudinal axis thereof parallel or substantially parallel to the longitudinal axis of cone 70. Channel 62 is adapted to receive and engage aiming bars 12 or 13 (see FIG. 2). Accordingly, an aiming bar held within channel 62 is maintained such as to orient its longitudinal axis substantially parallel to the longitudinal axis of cone 70. An aiming bar is held in position within channel 62 by set screw 64 which is threaded through the underside of channel 62 and bears against the outer surface of aiming bar 12 and 13. Stop means 15, which travel upon the aiming bars, are used to set the distance between cone 70 and film pouch 30. The actual location of the stop means 15 on the aiming bar is dependent upon the location of aiming bar locator means 60 on cone 70, the focal length of the x-ray camera and x-ray film quality.

The film holding apparatus is portable and free-standing (not wall positioned) and is maintained in position by means of a stand member (not shown). The upper portion 80 of the stand member (shown in cut-away position) is engaged within block 81. The film holder apparatus is locked into position atop stand member 80 by means of set screw 82.

In use, the film holder assembly is first adjusted to the proper height to accommodate a sitting or standing patient P. Three individual x-ray photographs are taken in sequence to secure the desired panoramic x-ray photograph. Each of the three x-ray photographs are secured by upwardly directing a beam of x-rays from x-ray unit 70 through the open ends of the patient's maxillary and mandibular arch structure to thereby expose the photographic plate enclosed within pouch 30. An x-ray photograph of the right side arch structure of the patient's maxillary and mandibular arches is secured by first raising aiming bar 13 from the rest position to the stop position. Thereafter, the x-ray camera is moved into position and aiming bar 13 inserted within channel 62 and held in position with set screw 64. This action serves to bring cone 70 into proper alignment to secure the desired x-ray photograph of the right side of the patient's maxillary and mandibular arch structure. The patient P positions himself before the open frontal portion of photograph plate holder assembly 20. The patient's chin should rest squarely on the upper surface of base member 10 (see FIG. 3). This position will place the zygomatic (cheek) bone in close proxmity to the photographic plate when the same is brought into position, as hereinafter described, and the lower border of the mandible will be approximately one inch further from the photographic plate than the cheek bone. Positioning member 50 is inserted between the upper and lower arches of patient P and defines the dental plane of occlusion. Positioning member 50 is preferably slidably or threadably connected to shield member 42 to facilitate removal for sterilization following use. Means may be provided for altering the height of the positioning member 50 from the upper surface of base member 10. As noted earlier, the positioning member can be attached to the upper surface of base member 10 rather than to shield member 42. For example, the positioning member 50 may comprise a plate member that extends upwardly and laterally from the upper surface of base member 10. The plate member may be inserted into the mouth of the patient and employed to fix the patient's head relative to the photographic plate contained within the film holder assembly.

Figure 4:
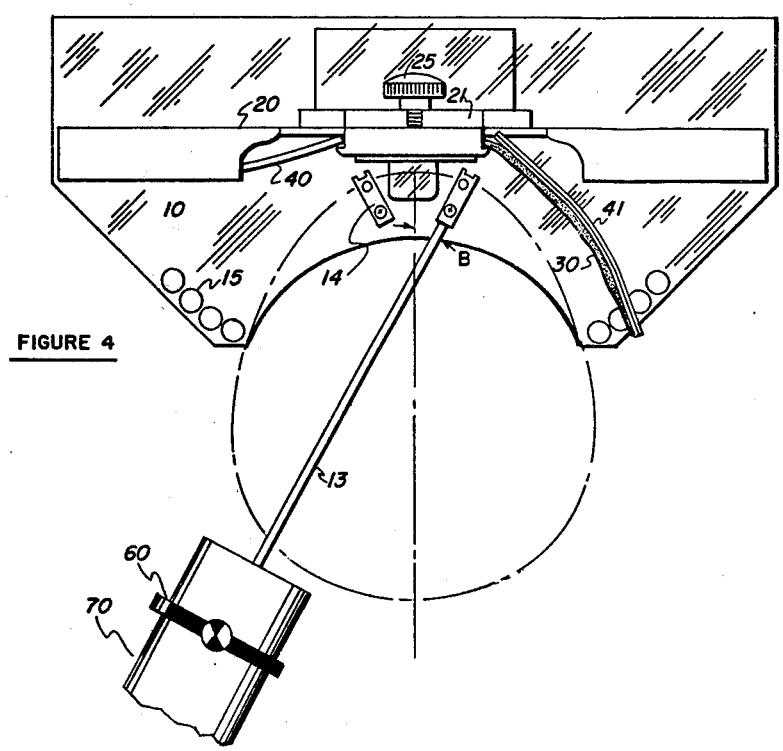
FIG. 4 is a horizontal top view of the assembly of the present invention.

After the patient is in position, a portion of film 30 is located in close proximity (preferably touching) the right side of the patient's face (see FIG. 4). This is accomplished by withdrawing side arch shield member 41 from its shielding positioned within downwardly extending lip 22. The side arch shield member is then rotated 180° and placed behind flexible pouch 30. The film pouch is maintained in position by engaging the lowermost portion of rod member 43 within a stop hole 15. Typically, one or more stop holes 15 are located in the upper surface of base member 10. Providing a number of stop holes at various distances from the central shield member permit the orthodontist to use the device with patients of widely varying head sizes and structures.

An x-ray beam is then directed upwardly through the open ends of the patient's arch structure. After the exposure is completed, set screw 64 is opened, the x-ray camera moved to withdraw aiming bar 13 from channel 62 and aiming bar 13 moved to the rest position. Then the shield member which served to support the photographic plate in an arch corresponding to the facial contour of the patient is removed, rotated and reinserted under lip 22 over the exposed portion of photograhic plate 30 by sliding bar member 43 within track guide 11 and downwardly extending lip 22 of the photograhic plate holder. The inward edge of shield members 40 and 41 are positioned in a lap joint relationship with the central plane shield member, that is, the inner edge of the side arch shield members are located behind the outer vertically extending edges of the central shield member.

To secure an x-ray photograph of the left side of the patient's arch structure, the x-ray camera and cone 70 is repositioned by raiding aiming bar 12 to the stop position (as in (FIG. 1) and inserting the terminal portion of the aiming bar into channel 62 up to the point where stop means 15 touches the forward-most portion of channel 62. Set screw 64 is closed fixing the position of the x-ray camera. Thereafter, patient P places himself before the positioned x-ray camera cone 70 and in front of central shield member 42. A portion of the photograhic plate is brought and maintained in close proximity to the left side of the patient's face utilizing side arch shield member 40. Upon completing the exposure set screw 64 is opened, the x-ray camera moved to withdraw aiming bar 12 from within channel 62 and aiming bar 12 dropped to the rest position. Shield member 40 is then returned to its original position as shown in FIG. 1.

The final x-ray photograph of the sagittal portion of the patient's arch structure is secured by positioning members 40 and 41 in shielding position and removing shield member 42 from its position over the photographic plate. The central shield member is slidably mounted from a central segment of the upper margin of the plate holder assembly 20 and extends downwardly over the planar member. Preferably, the central shield member rests on the upper surface of base member 10 and is located in shielding position by means of locking screw 25.

The photograph of the central portion of the arch structure is secured by directing the x-ray beam upwardly from below the plane of occlusion of the patient toward the anterior portion of the plane of occlusion at an angle of about 5° to 15°, preferably 10° below the horizontal. The cone of x-ray camera 70 is located against the nape of the patient's neck when the radiograph of the central portion of the patient's dental structure is secured. The cone of the camera is aligned with the unshielded portion of the film with the use of rod member 67 which is attached to aiming bar locator 60 by means of extension element 66. Rod member 67 is maintained in a position substantially parallel, vertically and horizontally, to the longitudinal axis of cone member 70. Preferably, rod member 67 is threaded into extension element 66 which in turn is held against and positioned upon aiming bar locator means 60 by set screw 65. The distance between the center-line of cone 70 and aiming bar 67 is equal to the distance between the center-line shield member 42 and the outer edge of plate holder 20. Proper alignment of the x-ray camera for obtaning a photograph of the central portion of the arch structure is ensured, after cone 70 is properly inclined against the patient's neck as specified before, by placing rod member 67 into notch 23 and having aiming rod 67 located substantially perpendicular to plate holder 20.

Exposure timing for each of the sequential x-rays is similar to standard extra oral procedures depending upon the strength of the x-ray tube (KVP and amperage) as well as illuminating screens employed, giving special consideration to the stature of the patient.

Following completion of the central photograph, the side arch shield members are removed and the photographic plate removed from within the plate holder assembly 20 and developed. As shown in the figures, the film holder apparatus of the present invention is independent of, that is, not permanently connected to, the x-ray camera employed in securing the desired exposures. Accordingly, the apparatus is readily portable.

What is claimed is:

1. An apparatus for producing in conjunction with and independent x-ray camera a panoramic x-ray photograph of dental arches on a photographic plate which comprises:
    (a) a base member having an upper and lower surface;
    (b) a planar photographic plate holder assembly perpendicularly affixed to the upper surface of said base member, the frontal portion of said holder assembly adapted to permit the exposure of a photographic plate positioned within said holder assembly;
    (c) a sectional overlapping shield assembly adapted to engage said holder assembly to cover a photographic plate positioned within said holder assembly to prevent the x-ray exposure of said photographic plate comprising at least one central shield member and said arch shield members located on each side of said central shield member;
    (d) means on said base member to alternatively position each of said side arch shield members and a photographic plate supported thereby in a non-shielded arch corresponding to the facial contour of a patient facing the holder assembly;
    (e) a positioning member located on said apparatus adapted to locate the upper and lower arches of said patient in a position facing and congruent with the frontal portion of said plate holder assembly;
    (f) means on said base member to locate said x-ray camera in photographing position and comprising left and right elongated aiming bars having their inner ends pivotably affixed to the lower surface of said base member, said aiming bars, in the rest position, extending downwardly from said base member, each of said aiming bars adapted to be swung upwardly from the rest position to a stop position, each of said aiming bars, at said stop position, forming an angle of about 15° below the horizontal and an angle of about 40° to 60° with an imaginary vertical plane bisecting said central shield member; and
    (g) aiming bar locator means located on the cone of said x-ray camera and adopted to engage a portion of said aiming bar when said aimming bar is in the stop position to thereby orient the longitudinal axis of said cone substantially parallel to the longitudinal axis of said aiming bar.

2. The apparatus of claim 1 wherein said base member is provided with means for positioning sais side arch shield members in close proximity to the upper and lower arch structure of a patient facing said holder assembly and in contact with said positioning member.

3. The apparatus of claim 1 wherein said plate holder assembly comprises a flat planar member that is provided with a downwardly extending lip member along at least a portion of the top margin thereof, said side arch shield members adapted to be slidably positioned under said lip member.

4. The apparatus of claim 1 wherein said aiming bar locator is provided with an elongated rod member that is spaced from said cone and maintained in a position substantially parallel, vertically and horizontally, to the longitudinal axis of said cone member.

* * * * *